US00PP31740P3

(12) United States Plant Patent
Gray et al.

(10) Patent No.: US PP31,740 P3
(45) Date of Patent: May 12, 2020

(54) FLORIBUNDA ROSE PLANT NAMED 'GRACHA'

(50) Latin Name: ***Rosa* hybrid**
Varietal Denomination: GRAcha

(71) Applicants: John Charles Gray, Highfields (AU); Sylvia Elizabeth Gray, Highfields (AU)

(72) Inventors: John Charles Gray, Highfields (AU); Sylvia Elizabeth Gray, Highfields (AU)

( * ) Notice: Subject to any disclaimer, the term of this patent is extended or adjusted under 35 U.S.C. 154(b) by 0 days.

(21) Appl. No.: 16/350,970

(22) Filed: Feb. 6, 2019

(65) Prior Publication Data

US 2019/0246531 P1 Aug. 8, 2019

Related U.S. Application Data

(60) Provisional application No. 62/626,746, filed on Feb. 6, 2018.

(51) Int. Cl.
*A01H 5/02* (2018.01)
*A01H 6/74* (2018.01)

(52) U.S. Cl.
USPC ..... Plt./148
CPC ..... *A01H 6/749* (2018.05)

(58) Field of Classification Search
USPC ..... Plt./148
See application file for complete search history.

*Primary Examiner* — Anne Marie Grunberg
(74) *Attorney, Agent, or Firm* — Samuel R. McCoy, Jr.

(57) ABSTRACT

'GRAcha' is a new and distinct floribunda type *Rosa* hybrid plant which is characterized by the combination of an upright to semi-weeping growth habit, very high resistance to *Diplocarpon rosae* and *Sphaerotheca pannosa*, nearly continuous flowering, electric mid pink double-type flowers, a strong rose fragrance, and the stability of these characteristics from generation to generation. The new cultivar is generally suited to landscape applications.

2 Drawing Sheets

Latin name of genus and species: The Latin name of the genus and species of the novel variety disclosed herein is *Rosa* hybrid.

Variety denomination: The inventive variety of *Rosa* hybrid disclosed herein has been given the variety denomination 'GRAcha'.

BACKGROUND OF THE INVENTION

Parentage: 'GRAcha' is a seedling selection which resulted from the controlled cross-pollination of an unnamed *Rosa* hybrid female breeding line (not patented) and an unnamed *Rosa* hybrid male breeding line (not patented). Both parents, developed by the same inventor and never commercially released, exhibited traits deemed commercially significant and desirable.

After many years of trialing, the female parent was confirmed to possess a combination of desirable traits such as complete resistance to rose black spot disease, complete resistance to powdery mildew, and flowers with a strong citrus-like perfume borne on a bushy plant growing to 1.2 m tall and wide. The male parent was selected for use in breeding after trialing confirmed the presence of strong true-rose perfume and a bright, modern flower color. During the summer of 2010, the female parent was emasculated and was manually pollinated with pollen from the male parent. In autumn of 2010, seed was collected from hips produced by the female parent and a number of seedlings were grown to a mature size, including the claimed plant. These progeny were further evaluated for desirable traits such as black spot disease resistance and strong perfume, and in June of 2011 the claimed plant was first observed. In January of 2013, after further evaluation for desirable traits, the claimed plant was deemed to be garden-worthy and suited to widespread cultivation. It was given the denomination, 'GRAcha'.

Asexual Reproduction: Asexual propagation of 'GRAcha', by way of softwood stem cuttings, was first performed in September of 2011 at the inventor's nursery in Highfields, Australia. Through more than twelve subsequent generations, the unique features of this cultivar have proven to be stable and true to type.

SUMMARY OF THE INVENTION

The following characteristics have been repeatedly observed and represent the distinguishing characteristics of the new *Rosa* cultivar 'GRAcha'. These traits, in combination, distinguish 'GRAcha' as a new and distinct cultivar.

1. *Rosa* hybrid 'GRAcha' exhibits an upright to semi-weeping growth habit; and
2. *Rosa* hybrid 'GRAcha' exhibits very high resistance to rose black spot disease (*Diplocarpon rosae*) and powdery mildew (*Sphaerotheca pannosa*); and
3. *Rosa* hybrid 'GRAcha' exhibits nearly continuous flowering; and
4. *Rosa* hybrid 'GRAcha' exhibits a very double flower type; and
5. *Rosa* hybrid 'GRAcha' exhibits electric pink flowers which fade to mauve pink; and
6. *Rosa* hybrid 'GRAcha' exhibits flowers with a strong rose fragrance.

DETAILED BOTANICAL DESCRIPTION

Figure 1:
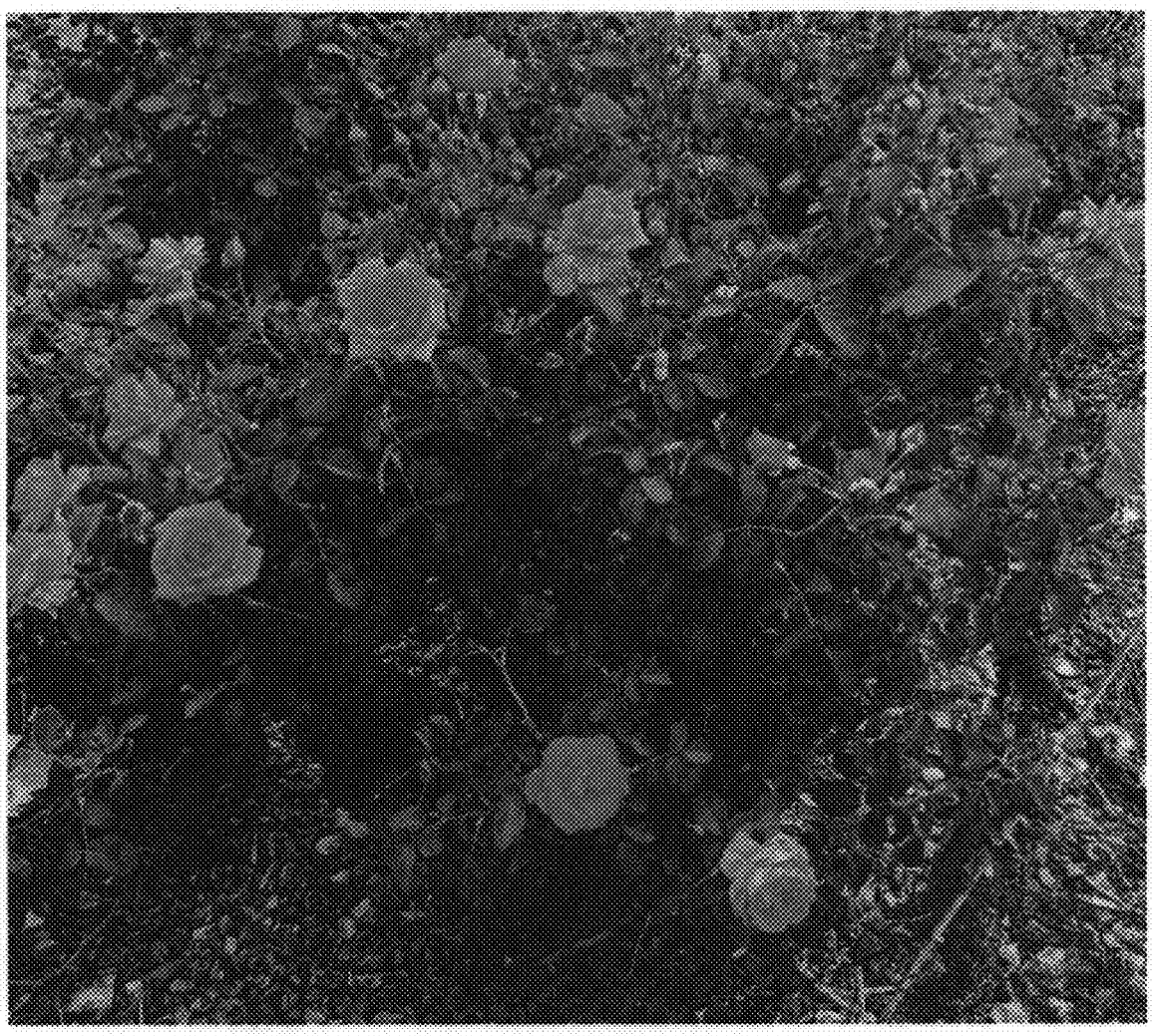
FIG. 1 illustrates, as nearly true as it is reasonably possible to make the same in color photographs of this type, an exemplary 24 month old 'GRAcha' plant grown outdoors at the inventor's commercial nursery in Highfields, Australia.
Figure 2:
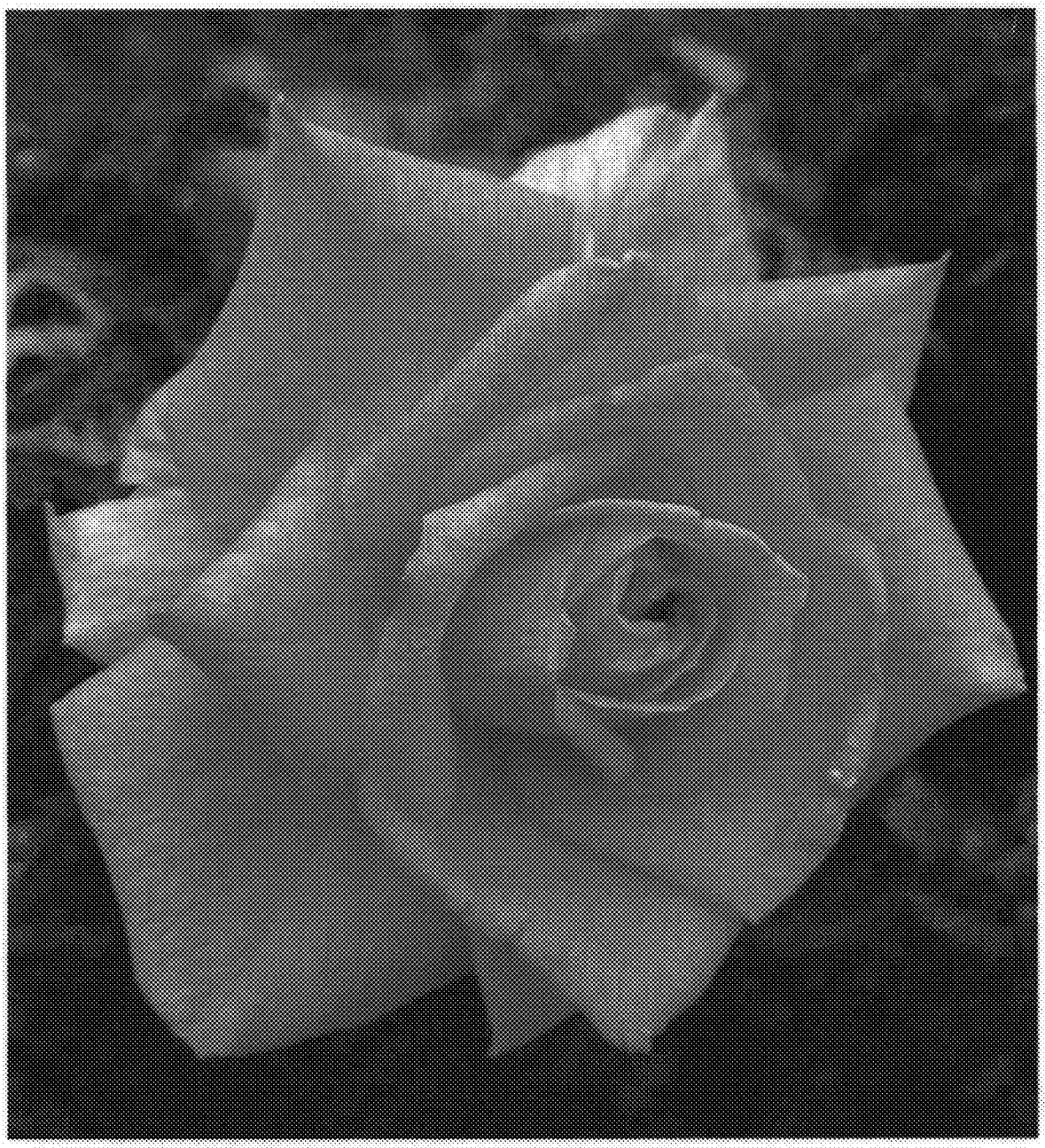
FIG. 2 illustrates, as nearly true as it is reasonably possible to make the same in color photographs of this type, the typical foliage and flower of 'GRAcha'.

The following observations and measurements, made in February of 2018, describe averages of two own-root specimens of one year old 'GRAcha' plants. The plants were grown outdoors in a garden bed of red krasnozem soil type, at the inventor's nursery in Highfields, Australia. No shade or supplemental light was provided. Temperatures ranged from approximately 17 to 35 degrees Celsius during the day and 7 to 18 degrees Celsius at night. Standard practices for irrigation, fertilizer and pest control were applied at appropriate times during the growing season. The plants were pruned three times during the growing season using accepted techniques for rose pruning.

Those skilled in the art will appreciate that certain characteristics will vary with older or, conversely, with younger plants. 'GRAcha' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2007 Fifth Edition except where common terms of color are used.

A botanical description of 'GRAcha' and comparisons with the parents and the most similar commercial cultivar of *Rosa* hybrid are provided below.

General plant description:

*Growth habit*.—Upright to semi-weeping.

*Growth rate*.—Approximately 1 years to reach 60 cm.

*Dimensions*.—120 cm tall and 100 cm wide.

*Environmental tolerance*.—Very good heat tolerance; cold hardiness is unknown.

*Disease resistance*.—Very high resistance to powdery mildew (*Sphaerotheca pannosa*) and blackspot (*Diplocarpon rosae*).

*Propagation*.—Technique — Softwood stem cuttings. Time to initiate roots — About 13 days at approximately 21 degrees Celsius at root zone and 18 degrees Celsius ambient temperature. Time to produce a rooted cutting — About 25 days at approximately 21 degrees Celsius at root zone and 18 degrees Celsius ambient temperature.

Root system: White fibrous roots with many root hairs extending from lesser roots in a featherlike arrangement.

Branches:

*Branching habit*.—Irregular branching from mature branches, breaking first from the uppermost buds near the apex of each shoot.

*Quantity*.—Numerous.

*General dimensions*.—Approximately 21 cm long; 0.7 cm in diameter near the base and tapering to 0.4 cm.

*Immature branches*.—Diameter — Approximately 0.7 cm. Texture and pubescence — Smooth with prickles. Color — Near RHS 142B.with anthocyanin present. Prickles — Density — Moderate.N43C. Shape — Convex. Texture — Smooth.

*Mature branches*.—Diameter — Approximately 0.7 cm, after one year. Texture and pubescence — Smooth with prickles; glabrous. Color — Near RHS 144D. Prickles — Density — Moderate. Color — Near RHS 29B. Shape — Convex. Texture — Smooth.

Leaves:

*Arrangement*.—Alternate imparipinnate compound leaves.

*Quantity*.—Approximately 10 per mature branch.

*Attachment*.—Petiolate.

*Leaf internode length*.—3.5 cm.

*Dimensions*.—Approximately 8 cm long and 7 cm wide.

*Petiole*.—Dimensions — Average of 3.0 cm long and 0.1 cm wide. Color — Near RHS 144C. Texture and pubescence — Rough and glabrous. Prickles — Small blunt prickle is present. Stipitate glands — Not present.

*Stipule*.—Dimensions — 1.5 cm long and 0.7 cm wide. Color — Near RHS 144A. Texture and pubescence — Smooth and glabrous. Margins — Ciliate. Apex — Apiculate. Base — winged. Prickles — Not present. Stipitate glands — Not present.

*Rachis*.—Dimensions — 2.0 cm long and 0.2 cm wide. Color — Near RHS 146B. Prickles — Present. Stipitate glands — Not present.

*Leaflets*.—Quantity — Five leaflets on axillary leaves. Dimensions — Average size of the terminal leaflet is 4.0 cm long and 3.0 cm wide. Shape — Ovate. Apex — Acuminate. Base — Ovate. Margins — Serrated. Texture, pubescence and luster, adaxial surface — Smooth, glabrous, and matte. Texture, pubescence and luster, abaxial surface — Rough, glabrous, and matte. Juvenile foliage color, adaxial surface — Near RHS 143A, with anthocyanin intonations, near RHS 53A, at the margins and midrib. Juvenile foliage color, abaxial surface — Near RHS 143D, with anthocyanin intonations, RHS 53A. Mature foliage color, adaxial surface — Near RHS N138A. Mature foliage color, abaxial surface — Near RHS 139D. Venation — Pinnate. Venation color, adaxial surface — Near RHS N141D. Venation color, abaxial surface — Near RHS 144C. Petiolule — Dimensions — 0.3 cm long and 0.1 cm wide. Color — Near RHS 144C. Prickles — Not present. Texture — Smooth.

Inflorescence:

*Inflorescence type*.—Terminal corymb consisting of approximately 2 to 6 pedicellate flowers.

*Blooming habit*.—Almost continuous from October through June in the southern hemisphere.

*Time to flower*.—6 to 8 weeks for a new stem to mature and flowering begins to occur once a stem matures.

*Dimensions*.—12 cm from the base of the lowest pedicel to the farthest distal flower and the width from farthest outstretched flower on one side of the inflorescence to the farthest outstretched flower on the opposite side is 18 cm.

*Peduncle*.—Dimensions — 5 cm long and 0.2 cm in diameter. Color — Near RHS 144D. Strength — Rigid. Texture and pubescence — Rough; with hairs. Prickles — None present.

Bud:

*Shape*.—Ovate.

*Size*.—2.5 cm long and 1.5 cm in diameter.

*Color*.—Near RHS 137D.

Flower:

*Pedicel*.—Dimensions — 5 cm. Color — Near RHS 144B. Strength — Rigid. Texture — Rough with hairs.

*Calyx*.—General — Comprised of five polysepalous sepals, with strong foliaceous appendages present on all sepals. Diameter of calyx — 0.8 cm. Sepals — Color, interior surface — RHS 144D. Color, exterior surface — RHS 144B. Dimensions — 2.0 cm long and 0.7 cm wide. Apex — Acuminate. Base — Flat at junction with receptacle. Quantity — Five. Pubescence — Densely puberulent. Margins — Two to three foliaceous appendages. Stipitate glands — None present.

*Corolla*.—General shape of corolla — Cupped and well-rounded at anthesis; aging to a flat whorl. Rate of opening — 6 days from bud to anthesis. Dimensions — Approximately 7 cm in diameter and 6 cm deep. Fragrance — Strong rose scent. Lastingness — On the plant for 5 days after anthesis. Persistence — Self-cleaning. Petals — Petal count — Exhibits very double flowers with approximately 70 petals under normal conditions. Petal arrangement — Irregularly rounded whorl, with loose outer whorl. Dimensions — 3.5 cm long and 3.0 cm wide. Petal shape — Obovate. Apex — Rounded to cordate. Base — Flattened, then obtuse. Petal reflex — Slightly reflexed at apex. Petal margin — Entire; slightly undulating. Texture — Soft. Aspect — Slightly ruffled. Petal color, upon opening — Upper surface — Near RHS N66B. Lower surface — Near RHS 64C. Petal color, at anthesis — Upper surface — Near RHS N66C. Lower surface — Near RHS 68D. Fading — Near RHS 65B.

Reproductive organs:

*Stamens*.—Quantity — Approximately 50. Anthers — Shape — Narrow ovate. Length — 0.1 cm. Color — Near RHS 21B. Pollen — Many. Pollen Color — Near RHS 3A. Filaments — Color — Near RHS 8D. Length — Approximately 0.7 cm.

*Pistils*.—Quantity — Approximately 50. Length — Approximately 0.8 cm. Stigma — Shape — Ovate. Color — Near RHS 11B. Style — Length — Approximately 0.3 cm long. Color — Near RHS 18D.

*Ovary*.—Dimensions — 0.5 cm long and 0.3 cm wide. Color — Near RHS 3D.

*Receptacle*.—Shape — Pitcher-shaped. Dimensions — 0.5 cm high and 0.5 cm wide. Color — Near RHS 137D.

Hip and seed:

*Hip*.—Shape — Rounded. Dimensions — 1.5 cm long and 1.5 cm wide. Texture — Smooth. Color — Near RHS 142B. Seed — Not present.

COMPARISONS WITH THE PARENTS

The new rose plant 'GRAcha' may be distinguished from its seed parent, an unnamed breeding line, by the following combination of characteristics:

1. The flowers of 'GRAcha' exhibit a distinct electric pink general tonality with a rounded form with a very large number pf petals forming a flattish whorl for some period of time after anthesis, whereas the flowers of the seed parent exhibit a soft pink general tonality and loose, open flowers.
2. 'GRAcha' exhibits an upright to semi-weeping growth habit, whereas the seed parent exhibits an upright growth habit.

The new rose plant 'GRAcha' may be distinguished from its pollen parent, an unnamed breeding line, by the following combination of characteristics:

1. The flowers of 'GRAdkpk' exhibit a distinct electric pink general tonality with a rounded form and center petals forming a flattish whorl for some period of time after anthesis, whereas the flowers of the pollen parent exhibit a purple general tonality.
2. 'GRAdkpk' exhibits an upright to semi-weeping growth habit, whereas the pollen parent exhibits an upright growth habit.
3. 'GRAdkpk' exhibits juvenile foliage colored near RHS 143A with anthocyanin intonations, whereas the pollen parent exhibits juvenile foliage colored near RHS 137C with no anthocyanin intonations.

COMPARISONS WITH THE MOST SIMILAR VARIETY OF COMMON KNOWLEDGE

Plants of the new cultivar 'GRAcha' may be distinguished from the commercial variety *Rosa* hybrid 'GRAppl' (U.S. Pat. No. 26,364) by the following combination of characteristics:

1. The flowers of 'GRAcha' exhibit a distinct electric pink general tonality, whereas the flowers of 'GRAppl' exhibit a purple general tonality.
2. 'GRAcha' exhibits a petal count of approximately 36 petals, whereas 'GRAppl' typically possesses 70 petals.
3. 'GRAcha' exhibits mature leaves that are strongly bullate whereas mature leaves of GRAppl are only slightly bullate.

That which is claimed:

1. A new and distinct variety of *Rosa* hybrid plant named 'GRAcha', as described and illustrated herein.

* * * * *